US007015484B2

(12) United States Patent
Gillispie et al.

(10) Patent No.: US 7,015,484 B2
(45) Date of Patent: Mar. 21, 2006

(54) MULTI-DIMENSIONAL FLUORESCENCE APPARATUS AND METHOD FOR RAPID AND HIGHLY SENSITIVE QUANTITATIVE ANALYSIS OF MIXTURES

(75) Inventors: Gregory Gillispie, Fargo, ND (US); Mark J. Pavicic, Fargo, ND (US)

(73) Assignee: Dakota Technologies, Inc., Fargo, ND (US)

( * ) Notice: Subject to any disclaimer, the term of this patent is extended or adjusted under 35 U.S.C. 154(b) by 108 days.

(21) Appl. No.: 10/431,347

(22) Filed: May 7, 2003

(65) Prior Publication Data

US 2004/0007675 A1 Jan. 15, 2004

Related U.S. Application Data

(63) Continuation-in-part of application No. 09/835,894, filed on Apr. 16, 2001, now abandoned.

(51) Int. Cl.
G01N 21/64 (2006.01)
(52) U.S. Cl. .................. 250/458.1; 250/459.1
(58) Field of Classification Search .......... 250/458.1, 250/459.1, 461.2; 356/328, 318, 334
See application file for complete search history.

(56) References Cited

U.S. PATENT DOCUMENTS

| 4,236,071 | A | | 11/1980 | Chimenti |
| 4,241,998 | A | | 12/1980 | Farkas et al. |
| 4,438,329 | A | | 3/1984 | Ford et al. |
| 4,791,310 | A | | 12/1988 | Honig et al. |
| 5,777,326 | A | * | 7/1998 | Rockwood et al. ......... 250/287 |
| 5,828,452 | A | | 10/1998 | Gillispie et al. |
| 5,912,257 | A | | 6/1999 | Prasad et al. |
| 5,955,737 | A | | 9/1999 | Hallidy et al. |
| 6,154,282 | A | | 11/2000 | Lilge et al. |
| 6,272,376 | B1 | | 8/2001 | Marcu et al. |
| 6,444,476 | B1 | | 9/2002 | Morgan |

FOREIGN PATENT DOCUMENTS

| GB | WO 99/63327 | * 12/1999 |
| WO | WO 99/63327 | 12/1999 |

OTHER PUBLICATIONS

"Mx4000 Multiplex Quantitative PCR System," *Biotechniques*, Stratagene®, 1 pg. (Feb. 2001).
"CompuScope 8500." GAGE Applied Sciences Inc., 4 pgs. (2000).
Bloch et al., "Field Test of a Novel Microlaser-Based Probe for in Situ Fluorescence Sensing of Soil Contamination," *Applied Spectroscopy*, 52(10):1299-1304 (1998).

(Continued)

*Primary Examiner*—Otilia Gabor
(74) *Attorney, Agent, or Firm*—Leffert Jay & Polglaze, P.A.

(57) ABSTRACT

Apparatus and methods are provided for rapid and sensitive quantitative analysis of a sample's fluorescence decay properties. A repetitively pulsed excitation light source generates pulsed fluorescence in the sample. A fluorescence wavelength selector receives a portion of the pulsed fluorescence emanating from the sample and outputs fluorescence photons whose wavelengths lie within a specified wavelength range. A photodetector receives the fluorescence photons within the specified wavelength range as an input from the fluorescence wavelength selector and outputs a time-dependent electrical signal. An array of memory elements stores a representation of the time-dependent electrical signal as a time-series of analog voltages or charges. Successive elements in the array correspond to a time increment of no greater than 4 ns. An analog-to-digital converter transforms the time-series of analog voltages or charges into a corresponding digitized fluorescence waveform.

36 Claims, 7 Drawing Sheets

OTHER PUBLICATIONS

Burt et al., "On-the-Fly Fluorescence Lifetime Detection in Liquid Chromatography with Data Collected Simultaneously at Multiple Emission Wavelengths," *Applied Spectroscopy*, 53(12):1496-1501 (1999).

Dvorak et al., "On-theFly Fluorescence Lifetime Determination with Total Emission Detection in HPLC," *Analytical Chemistry*, 69(17):3458-3464 (1997).

Gillispie et al., "Subsurface Optical Probes: Current Status and Future Prospects," *Proceedings of the 1993 U.S. EPA/A&WMA Int'l Symposium on "Field Screening Methods for Hazardous Wastes and Toxic Chemicals"*, Las Vegas, pp. 793-805 (1993).

He et al., "On-the-Fly Fluorescence Lifetime Detection of Dye-Labeled DNA Primers for Multiplex Analysis," *Analytical Chemistry*, 70:3413-3418 (1998).

Knorr et al., "Resolution of Multicomponent Fluorescence Spectra by an Emission Wavelength—Decay Time Data Matrix," *Analytical Chemistry*, 53:272-276 (1981).

Meidinger et al., "Fluorescence of Aromatic Hydrocarbons in Aqueous Solution," *Proceedings of the 1993 U.S. EPA/A&WMA Int'l Symposium on "Field Screening Methods for Hazardous Wastes and Toxic Chemicals"*, Las Vegas, pp. 395-403 (1993).

Panne et al., "A fiber-optical sensor for polynuclear aromatic hydrocarbons based on multidimensional fluorescence," *Sensors and Actuators B*, 13-14:288-292 (1993).

St. Germain et al., "Real-Time Continuous Measurement of Subsurface Petroleum Contamination with the Rapid Optical Screening Tool (ROST™)," *Proceedings of the 1995 U.S. EPA/A&WMA Int'l Symposium on Field Screening Methods for Hazardous Wastes and Toxic Chemicals*, (11 sheets) (1995).

St. Germain et al., "Variable Wavelength Laser System for Field Fluorescence Measurements," *Proceedings of the 1993 U.S. EPA/A&WMA Int'l Symposium on "Field Screening Methods for Hazardous Wastes and Toxic Chemicals"*, Las Vegas, pp. 1113-1122 (1993).

Soper et al., "On-Line Fluorescence Lifetime Determinations in Capillary Electrophoresis," *Analytical Chemistry*, 67:4358-4365 (1995).

* cited by examiner

MULTI-DIMENSIONAL FLUORESCENCE APPARATUS AND METHOD FOR RAPID AND HIGHLY SENSITIVE QUANTITATIVE ANALYSIS OF MIXTURES

CROSS REFERENCE TO RELATED APPLICATIONS

This Application is a Continuation-in-Part of U.S. application Ser. No. 09/835,894 filed Apr. 16, 2001 now abandoned, which application is incorporated herein by reference.

TECHNICAL FIELD

The present invention relates generally to the field of fluorometry and, in particular, to an apparatus that rapidly gathers fluorescence decay data generated by a pulsed excitation source.

BACKGROUND

Instruments designed to gather precise fluorescence intensity data are commonly referred to as fluorometers (also known as fluorimeters). The fluorometers found in high performance liquid chromatography (HPLC), capillary electrophoresis (CE), and automated DNA sequencing instruments are also referred to simply as fluorescence detectors. Conceptually similar fluorescence detectors are employed in microwell plate readers and microarray scanners. Other quantitative analysis applications of fluorometers include counting cells via flow cytometry, determining the amount of DNA or RNA in a sample, measuring enzyme activity, and determining concentrations of hydrocarbons or chlorophyll in water.

Fluorometric apparatuses can be differentiated by the nature of the sample, how the sample is presented to the fluorometer, and the type of fluorescence data that is gathered. In order to fully comprehend our invention and its significance, one must recognize and understand the strengths and weaknesses of the many known variations of fluorometers. At a minimum, every fluorometer incorporates an excitation light source that serves to induce fluorescence in the sample, a means to isolate only those fluorescence photons with a specified wavelength range, and a photodetector that converts the fluorescence light flux within the selected wavelength range to an analog electrical signal; many fluorometers have provision for converting the analog electrical signal to a digitized representation that can be read visually or stored for subsequent data analysis.

The process of fluorescence is initiated when molecules in the sample absorb photons from the light source. The energy that was carried by the excitation photons is transferred to the molecules, thereby creating a population of electronically excited molecules. The molecules cannot remain in these excited states indefinitely owing to several possible de-excitation pathways, one of which is photon emission (fluorescence). Owing to certain vibrational relaxation and internal conversion processes that occur between the act of photon absorption (excitation) and photon emission (fluorescence), the average wavelength of the emitted photons is invariably longer than the excitation wavelength that was used to create the excited states via photoabsorption. Within a few picoseconds of the time an excited state molecule is created, it relaxes to the first excited singlet state and it is from this state that the fluorescence occurs. The average residence time of the molecule in the first excited singlet state in usually on the order of 0.1–100 nanoseconds. The shape of the fluorescence spectrum (but not the total intensity) for any particular compound is nearly the same regardless of the choice of excitation wavelength. Likewise, the shape of the excitation spectrum (but not the total intensity) of any particular compound is nearly the same regardless of the choice of wavelength at which the emission is monitored.

Many different excitation sources can supply the more or less monochromatic incident beam of light that is needed to excite (induce) fluorescence in the sample. Some excitation light sources, including tungsten or quartz-halogen lamps, xenon arc lamps, and xenon flashlamps, emit photons over such a broad range of wavelengths so as to require that an interference filter, monochromator, or other wavelength-selector be interposed between the excitation light source and the sample. The primary purpose of the excitation wavelength-selector is to prevent scattered excitation photons whose wavelength is the same as the fluorescence signal of interest from entering the detection system. The output of medium or high pressure xenon arc lamps and xenon flashlamps covers from the vacuum ultraviolet (wavelengths shorter than 200 nm) through the ultraviolet and visible regions and into the near-infrared; thus, essentially any desired wavelength can be obtained by appropriate choice of the excitation wavelength selector, albeit at the price of having to discard 99% or more of the photons emerging from the excitation light source. Light emitting diodes (LEDs) provide photons in comparatively narrower wavelength ranges, 50–100 nm, which eases the task for wavelength filtering their output. Inexpensive LEDs that span the wavelength range from approximately 360 nm into the near-infrared are commercially available.

Laser excitation sources can be highly advantageous for fluorometer applications because their output is so highly monochromatic and the laser light can easily be directed to and focused on the desired sample location. The laser sources that are found in nearly all automated DNA analyzers and most microarray readers generally provide photons in a single, very narrow wavelength range. In order to retain at least a portion of the valuable information that is inherent in the dependence of the fluorescence intensity on excitation wavelength, such instruments may incorporate several fixed wavelength laser sources, although this increases complexity, cost, and measurement time. Tunable lasers or optical parametric oscillators (OPOs) are coherent sources whose output wavelength is continuously variable, but they are also generally large and expensive.

The fluorescence intensity can be monitored within a single emission wavelength range, at several discrete emission wavelengths, or over a continuous range of wavelengths. Instruments that employ dielectric interference filters or glass cut-off filters to select the emission monitoring wavelengths are generally referred to as fluorometers or fluorimeters. The operator may be required to select and install a different filter in the instrument every time the wavelength at which the emission is monitored is changed. Versions with several filters installed in a rotatable filter wheel or on a filter slide, which could be either manually controlled or attached to a motor, are more convenient. Monochromators are very flexible and versatile instruments for wavelength selection. Adjusting the position of a grating or prism within the monochromator allows continuous variation of the passband wavelength. The width of the passband is similarly adjustable through control of the entrance and exit slit widths. Fluorescence measurement instruments that incorporate scanning monochromators for continuous variation of the emission wavelength or both the excitation and emission wavelength are generally referred to as spectrofluorometers or spectrofluorimeters. Yet another option is to use an array detector such as a charge-coupled device (CCD) camera to collect the entire fluorescence spectrum at once. In this case, the monochromator that is used to disperse (spatially separate) the fluorescence is commonly referred to as a spectrograph. Well-known procedures can be applied to correct the experimental emission spectrum and the excitation spectrum for the wavelength dependence of the measurement system. The corrected spectra then represent fundamental fluorescence properties of the molecules, although these properties may exhibit some dependence on the molecular environment; e.g., the fluorescence spectrum could shift in wavelength if the polarity of the solvent is varied. The practice and principles of fluorescence spectroscopy are described in many textbooks and reference books.

Fluorescence lifetime is another molecular property that is less affected by details of the measurement system than is the case for the spectra. For example, the fluorescence lifetime does not change when the amount of light directed onto the sample is reduced with a neutral density filter, after a change in excitation wavelength, or if the pulse repetition frequency of the light source is varied. The individual excited state persistence times for a population of identically prepared molecules is statistically distributed, but the decay of the collective excited state population follows so-called first order kinetics or exponential decay. The lifetime is the time interval over which the excited state population falls to $1/e=36.8\%$ of its initial population. The excited state lifetime is related to the rate constants for all process that deactivate the excited state, but it is commonly referred to as the fluorescence lifetime because fluorescence is by far the most convenient way to follow the changes in excited state population.

Little or no fluorescence lifetime information can be gained if the intensity of the excitation beam directed on to the sample is essentially constant. One means of obtaining lifetime information is to temporally modulate the intensity of the excitation light, usually in a sinusoidal pattern. The emission response of the sample necessarily has the same modulation frequency as the excitation. However, the inherent time lag between the excitation and emission processes induces a phase shift that is mathematically related to the fluorescence lifetime. Such techniques are commonly referred to as frequency domain spectroscopy.

A conceptually simpler approach is to excite the fluorescence with a light pulse of short duration and to measure the temporal pattern of the subsequent fluorescence. The entire fluorescence decay curve can be measured following a single laser excitation pulse with a digital oscilloscope or transient digitizer, whose function is to track the output of a photomultiplier tube or other photodetector at closely-spaced time intervals. A plot of fluorescence intensity vs. time interval expressed relative to the time at which the excited state population is generated is commonly referred to as a fluorescence decay curve; a digitized representation of a transient signal as a function of time is also commonly referred to as a waveform or profile. In the ideal case that the time duration (pulse width) of the excitation pulse is much shorter than the fluorescence decay time, the lifetime can be determined from a plot of $\ln I_t$ vs. $t$ where $I_t$ is fluorescence intensity at-time $t$ relative to the laser pulse. Many mathematical deconvolution techniques are available for situations in which the excitation pulse duration is not infinitesimally short compared to the fluorescence lifetime. Deconvolution techniques require that the intensity be measured as a function of time for both the excitation pulse and the subsequent fluorescence pulse. Apart from a relatively uninteresting multiplicative factor, the mathematical relationship between the fluorescence and excitation waveforms involves a single parameter, namely the fluorescence lifetime. Each deconvolution procedure has the same goal, namely to determine the value of the lifetime that gives the best fit between the observed and predicted fluorescence decay curves.

The statement above that the fluorescence lifetime is independent of the emission monitoring wavelength is not necessarily true for mixtures. The apparent fluorescence lifetime will depend on the excitation or fluorescence wavelength if the sample contains multiple emitting species with different lifetimes and different excitation and emission spectra. In such cases, one expects to observe bi-exponential or multi-exponential decay. The invariance of the fluorescence lifetime to excitation or emission wavelength is a test of sample purity, similar to tests based on the invariance of the excitation spectrum to emission monitoring wavelength and the invariance of the emission spectrum to excitation wavelength. The mathematical data processing techniques, including deconvolution, are readily generalized to account for multiple emitting species.

The traditional way to gather the fluorescence decay curve (and the laser excitation pulse shape, if needed for deconvolution) is via time-correlated single photon counting (TC-SPC). In TCSPC the sample is repetitively excited and a histogram of the time interval between when the sample is excited and when the first fluorescence photon is detected is generated. The histogram is functionally equivalent to the fluorescence decay curve that can be measured with a transient digitizer. The data contained within the TC-SPC histogram follow so-called Poisson statistics. On the other hand, in order to attain the condition of Poisson statistics, the measurement conditions must be arranged so that an actual datum (one point in the histogram) is collected on no more than 1 or 2 percent of the laser pulses. Thus, data collection is a lengthy and inefficient process.

Fluorometry often provides higher measurement sensitivity and specificity, greater ease of operation, faster measurement time, or lower instrumentation cost in comparison to other instrumental techniques. Fluorescence spectroscopy is inherently sensitive because the signals of interest are measured against a low (ideally zero) background signal. Absorption spectroscopy, in contrast, is less sensitive when operating near the limit of detection or limit of quantitation because a very small decrease in a large light signal must be determined. The unique combination of excitation spectrum, emission spectrum, and lifetime possessed by each fluorescent compound provides the specificity.

The fluorescent signal intensity depends, inter alia, on the flux of excitation photons within the sample volume and the number of fluorophores within that volume. Other factors that influence the total fluorescence intensity are the wavelength-dependent responses of the wavelength analyzer and the photodetector, the optics used to deliver the excitation light to the sample, the optics used to deliver a portion of the emitted light to the wavelength analyzer in front of the photodetector; and the specific geometrical arrangement of the light source, excitation optics, collection optics, and wavelength analyzer. The fluorescence intensity thus depends on inherent spectroscopic properties of the potentially fluorescent molecules (fluorophores), on the concentration of fluorophores, and on properties of the measurement system itself.

The procedures for characterizing the measurement system properties are tedious and time consuming. Therefore, for purposes of quantitative analysis one generally compares the fluorescence intensity of the sample to the fluorescence intensities of reference or standard samples whose concentrations are known. If the sample consists of a fluid solution, the concentration is usually expressed as a mass per unit volume. For fluorescent species arrayed on a surface, the amount would likely be expressed in terms of mass per unit area. Therefore, fluorescence induced in a sample makes it possible to identify if a fluorescent compound is present in a sample (qualitative analysis) and, if so, to determine its concentration or amount (quantitative analysis).

If it is known that the sample fluorescence intensity arises from a single, known compound, implementation of the quantitative analysis techniques and interpretation of the data are straightforward. The quality and value of the analysis is compromised if the sample contains unknown or unsuspected fluorescent species or if the fluorescence data are corrupted by interfering background signals. Fluorescence is ideally a zero background technique, as was stated above, but a certain amount of background signal is inevitably present. The sources of the background signal are many, including stray excitation light at the desired fluorescence monitoring wavelength, fluorescence from impurities in the sample, and interfering fluorescence of the sample container.

A high data acquisition rate is essential for most chromatographic analyses, microplate or microarray scanning, in vivo optical diagnostics, and many other procedures in which either the sample composition is rapidly changing or many different samples must be tested. How to account for background signal and how to sense when more than one species is contributing to the fluorescence signal is a common theme and challenge. Confirmatory chemical analysis by techniques that rely on discrete sampling are so time consuming as to be completely incompatible with the desire for rapid measurement rate.

A primitive approach that has some value for chromatography is to examine the pattern of intensities at contiguous elution times. The fluorescence intensity of a species as it elutes is expected to vary smoothly from zero to a maximum and then return to zero. Various mathematical formulas have been postulated to fit the shapes of the peaks, which are referred to by such terms as normal (Gaussian) or log-normal; sufficiently large deviations from the characteristic shape for compounds eluting at comparable time intervals after the sample was injected could signify the presence of two or more fluorophores whose peaks are overlapping. As long as the sample concentrations are low enough so that energy transfer and quenching processes are negligible, the total fluorescence intensity is closely approximated by the sum of contributions from the individual fluorescent compounds in the sample. The sample conditions that apply to high performance liquid chromatography (HPLC) and capillary electrophoresis (CE), for DNA sequencing analysis, and for many other fluorescence procedures satisfy the dilute sample condition requirement. Thus, one can attempt to resolve the overlapping peaks, but procedures that attempt to do so solely on the basis of lineshape are notoriously inaccurate. Nor does such an analysis provide any information on the chemical identity of an interfering fluorophore. Background subtraction techniques that assume that the background signal is either constant or slowly varying are similarly applied and have similar limitations.

There is precedent for using spectroscopic data in more elaborate fashion to test for peak purity. For example, photodiode array (PDA) detectors that can measure a full absorption spectrum, as opposed to absorbance at a single wavelength, are well known in chromatography. Peaks can be tentatively assigned and peak purity assessed by comparing the measured spectrum at a given elution time to the entries in a database of known standard spectra. A peak purity index is derived from the degree of overlap of the unknown spectrum with its closest match in the database. However, if the peak purity index is low, suggesting that there is more than one emitting component in the sample, the problem of how to apportion the total spectrum into its components, including background signal, remains. Thus, PDA detectors are used more to avoid misassignments than it is to increase the amount of information that can be gained in a given amount of experiment time.

Owing to the cumbersome nature of the peak purity testing procedures and the lack of easily applied algorithms that can accurately resolve overlapping peaks into the contributions of individual species, great effort is undertaken to arrange the chromatographic separation conditions to reduce the likelihood that more than one kind of species is in the detector volume at a given time. Unfortunately, these conditions, which require careful optimization and adjustment of variables such as the solvent's eluting strength and the flow rate, invariably result in much longer elution times and diminished productivity.

In fact, virtually all fluorescence detectors used in chromatography, microplate readers, microarray readers, quantitative PCR apparatuses, etc., rely on measuring with a single excitation wavelength and a single emission wavelength for each sample composition or location because this is the only approach compatible with the high data acquisition rates. One must recognize that the datum from such a measurement is simply a number, regardless of the units in which it is expressed, e.g., current, voltage, counts, etc. The data are dimensionally zero-order in mathematical terms. It should be apparent that unambiguously decomposing this number into the separate contributions of different fluorophores or a fluorophore and background is impossible. From the standpoint of purity, it is similarly impossible mathematically to assign a purity index to the individual measurement.

The only fluorescence detectors that routinely collect a full fluorescence spectrum at closely spaced time intervals, e.g., less than one second, are found in very expensive automated DNA sequencers. The most sophisticated of these sequencers collect the entire fluorescence spectrum with a CCD camera positioned at the exit focal plane of a spectrograph, but most of the spectral information is discarded in the data processing step. Other versions make measurements at a multiplicity of wavelengths (typically four because four dyes are used in one-lane DNA sequencing) via rapid rotation of a filter wheel or the use of dichroic filters to direct the light in various wavelength ranges to multiple detectors. Certain microplate and microarray readers allow either the emission monochromator or excitation monochromator to be scanned to generate a full spectrum, but these modes are too slow for most applications.

Fluorescence potentially offers many different options (none of which are routinely used) for confidence testing analogous to the use of a PDA in absorbance detection for HPLC. The analogy would be closest if a complete fluorescence spectrum were measured at each elution time in the chromatogram, which could be accomplished with an intensified photodiode array (IPDA), also referred to as a gated optical multichannel analyzer (OMA). Alternatively, a CCD camera detector with elements binned along an axis perpendicular to the spectral dispersion direction could be used to collect a full fluorescence spectrum. Although such implementations have been described in the literature, their use has been limited to research purposes because of high cost and other reasons.

There is ample evidence in the literature and widespread agreement among researchers that multidimensional fluorescence analyses yield much more information in terms of both specificity and sensitivity than corresponding one-dimensional spectral techniques. However, the use of multidimensional techniques has largely been limited to research investigations because: 1) The rate at which the data are gathered and processed is generally far too slow for any practical commercial application; 2) Technologies that could achieve the requisite speed are prohibitively expensive; and 3) Robust and rapid data analysis methodologies are not available to utilize the information that is inherently contained in the data. Attempts at commercialization of the technology and methodology have been hampered by these impediments.

Fluorescence is unique among spectroscopic techniques in its capability for multidimensional data wherein fluorescence intensity data are measured along at least two of the three important spectroscopic coordinates, which are excitation wavelength, emission wavelength, and fluorescence decay time. The most familiar multi-dimensional fluorescence representation is that of an excitation-emission matrix (EEM). EEMs are most commonly generated as a series of emission spectra acquired at different excitation wavelengths. Alternatively and equivalently, a series of excitation spectra can be gathered for different emission monitoring wavelengths and will yield the same result. By their very nature, EEMs contain more information than is available in either the excitation or the emission spectrum alone. The potential benefits of EEMs for purposes of diagnosing tumors via endoscopy or identifying sources of oil spills have long been recognized. However, the practical use of EEMs has been severely circumscribed by the lengthy and tedious manner in which they must be acquired.

At least two groups have proposed speeding the process by which EEMs are collected using a multiple wavelength excitation source based on Raman shifting, but these are complicated instruments requiring separate pairs of optical fibers for every excitation wavelength and an expensive CCD camera. Moreover, the Raman shifting process leads to large fluctuations in the laser excitation pulse energy and degraded signal to noise. A company has recently introduced a commercial fluorimeter that incorporates an old technique known as video fluorometry, allowing the collection of an EEM in as short a time as one second. However, the fast measurement time comes at a ten-fold or greater sacrifice in measurement sensitivity and the question of how to analyze the data remains.

Decomposing the sample's total emission or excitation spectrum into contributions from its various constituents is difficult. If a pulsed excitation source of sufficiently short duration is employed, one can collect second-order data in the form of a wavelength-time matrix (WTM). A WTM in its simplest incarnation consists of fluorescence decay curves measured at a series of emission or excitation wavelengths. The information can be assembled into a two-dimensional data array in which the columns represent different wavelengths (either excitation or emission), and the rows represent different time increments relative to the time at which fluorescence was excited with a short duration laser pulse. Although WTMs have received far less attention in the literature than EEMs, they possess certain advantages owing to the manner in which the fluorescence decay curves can be mathematically related to the laser excitation waveforms.

If EEMs or WTMs are collected in sequence mode, i.e., one emission spectrum or one fluorescence decay curve at a time, it is very important that conditions be held as constant as possible during the entire sequence to avoid distortion. The shorter the measurement time for a fluorescence decay curve, the easier it is to approach the case of constant sample conditions. Two likely sources of distortion are drifts in the laser power or sample degradation. For example, if the laser intensity steadily dropped during the collection of the EEM, then there will be a systematic error across the EEM. The same type of behavior results if photochemistry or other processes change the concentration of fluorophores in the sample during the course of the data collection. These problems are avoided if the entire EEM or WTM can be collected simultaneously.

Heretofore, instruments used for generating WTMs have been too slow and unstable to be useful for many analytical processes, such as analysis of samples whose properties change rapidly in time and space, including analysis of flowing fluids or rapidly scanning sample surfaces. The reasons for this situation are many and varied, but include shot-to-shot laser fluctuation, slow repetition rates and expense of the lasers, inability of digitizers to keep pace with lasers having faster repetition rates, lack of methodology for handling the volume of data generated, and lack of robust algorithms for analysis of the data.

Our invention solves numerous problems related to the pervasive and challenging situation in which the sample contains multiple fluorescent compounds.

SUMMARY

One embodiment of the present invention provides an apparatus that provides rapid and sensitive quantitative analysis of a sample's fluorescence decay properties. The apparatus has a repetitively pulsed excitation light source for generating excitation light pulses, an output of which generates pulsed fluorescence in the sample. Also included is a fluorescence wavelength selector that receives as input a portion of the pulsed fluorescence emanating from the sample and that outputs fluorescence photons whose wavelengths lie within a specified wavelength range. A photodetector that receives the fluorescence photons within the specified wavelength range as an input from the fluorescence wavelength selector and outputs a time-dependent electrical signal is included in the apparatus. The apparatus includes an array of memory elements that stores a representation of the time-dependent electrical signal as a time-series of analog voltages or charges. Successive elements in the array correspond to a time increment of no greater than 4 ns. The apparatus further includes an analog-to-digital converter that transforms the time-series of analog voltages or charges into a corresponding digitized fluorescence waveform.

DETAILED DESCRIPTION

In the following detailed description, reference is made to the accompanying drawings that form a part hereof, and in which is shown by way of illustration specific illustrative embodiments in which the invention may be practiced. These embodiments are described in sufficient detail to enable those skilled in the art to practice the invention, and it is to be understood that other embodiments may be utilized and that logical, mechanical and electrical changes may be made without departing from the spirit and scope of the present invention. The following detailed description is, therefore, not to be taken in a limiting sense.

Figure 1:
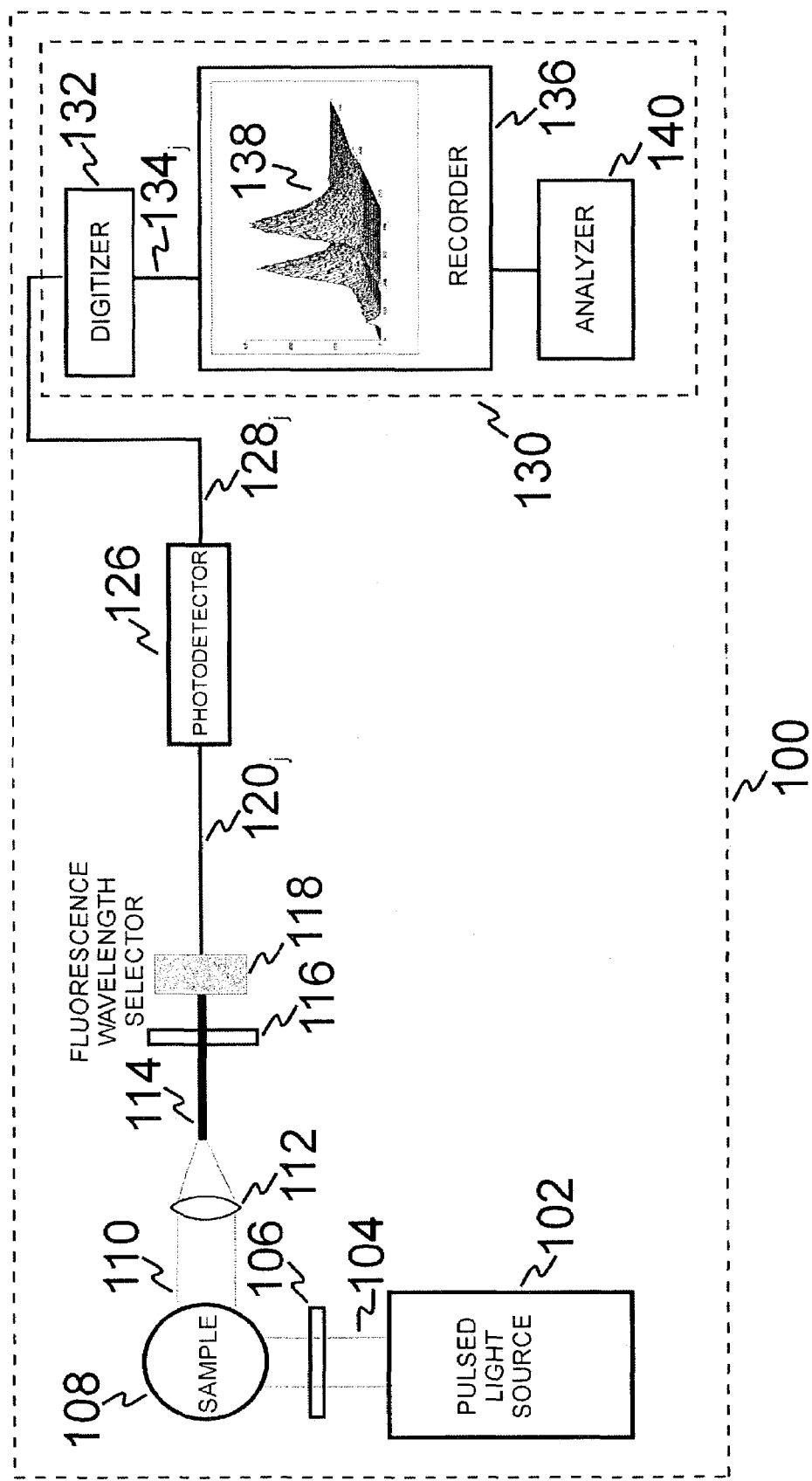
FIG. 1 is a block diagram illustrating an embodiment of the present invention.

Apparatus 100, shown in FIG. 1, demonstrates an embodiment of the present invention. Apparatus 100 includes pulsed light source 102, which emits beam 104 as a repetitive stream of light pulses. The wavelength of beam 104 is suitable to excite fluorescence in a sample. The duration of the light pulses, as measured by the full temporal width of the pulses at half the maximum intensity, is less than 1 nanoseconds. The root-mean-square deviation in the pulse energy, commonly referred to as the shot-to-shot fluctuation, is no greater than one percent for pulsed light source 102. Pulsed light source 102 is adapted to emit 100 or more pulses each second.

In one embodiment, pulsed light source 102 is a single-mode pulsed laser, e.g., the passively Q-switched, solid-state Nd: YAG laser manufactured by Litton Airtron Synoptics (Model ML-00024) or by JDS Uniphase (NanoLaser). Excitation light source 102 can be adapted to output light as the second harmonic (532 nm), third harmonic (355 nm), or fourth harmonic (266 nm) with the aid of appropriate non-linear optical materials whose use is familiar to those of ordinary skill in the art. Single mode in this context refers to the longitudinal mode structure, single mode being desirable because the intensity of the light pulse is temporally smooth, i.e., the intensity monotonically increases to a maximum value, then monotonically decreases without exhibiting secondary intensity maxima or minima.

Figure 2A:
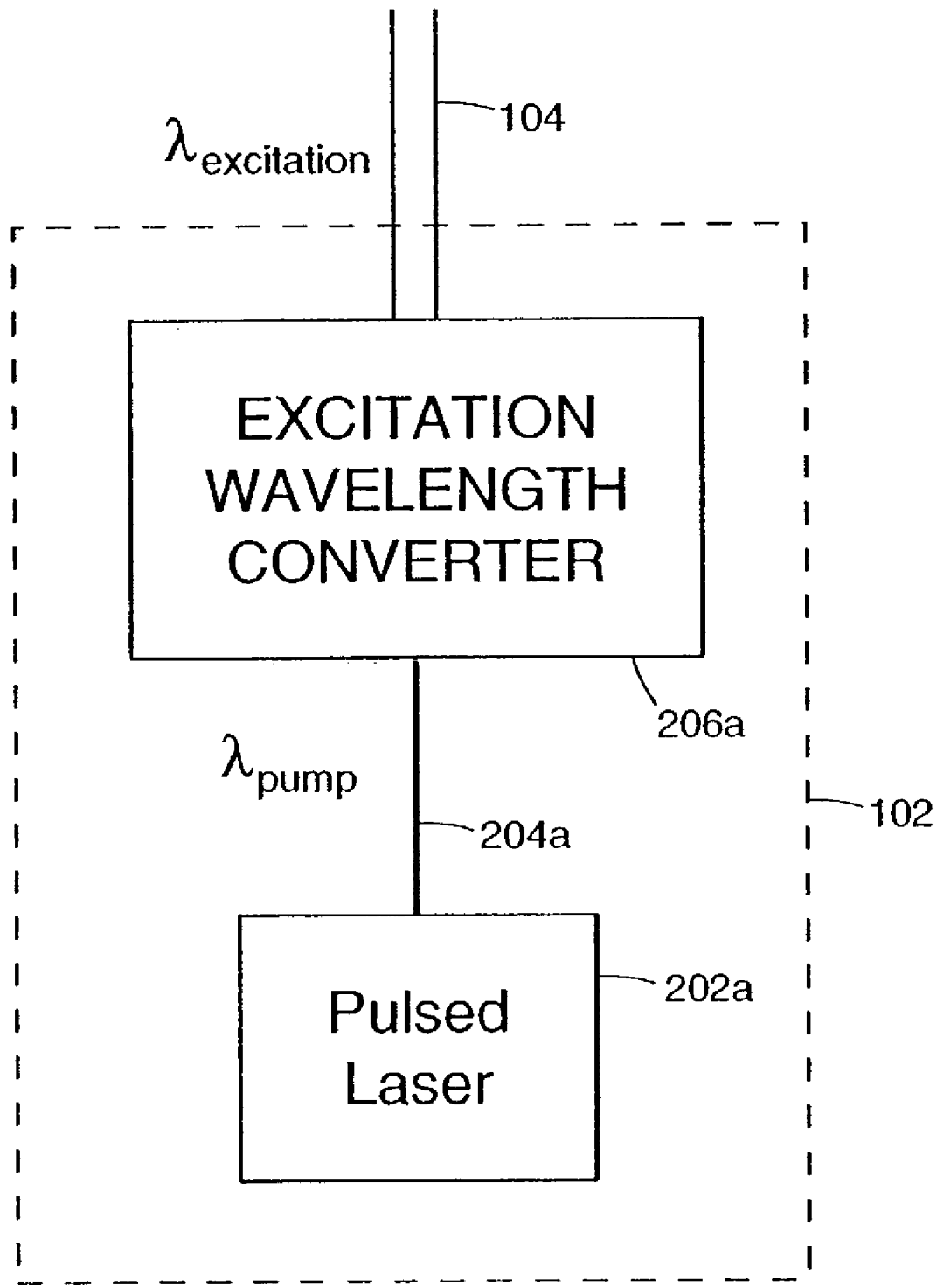
FIGS. 2a and 2b are block diagrams respectively illustrating different embodiments of a pulsed light source according to the teachings of the present invention.

In other embodiments, pulsed light source 102 is adapted to selectively output excitation beam 104 at various wavelengths that can be selected by the user. In the embodiment shown in FIG. 2a, pulsed light source 102 includes input pulsed laser 202a that directs pump beam 204a to excitation wavelength-converter 206a. Excitation wavelength-converter 206a receives the photons in beam 204a at wavelength $\lambda_{pump}$ and converts a fraction of the received photons to photons at a different wavelength $\lambda_{excitation}$. Various wavelengths are selectively output by selecting different values for $\lambda_{excitation}$ at excitation wavelength-converter 206a. Excitation wavelength-converter 206 can be a dye laser, a solid-state vibronic laser, an optical parametric oscillator, or the like.

Figure 2B:
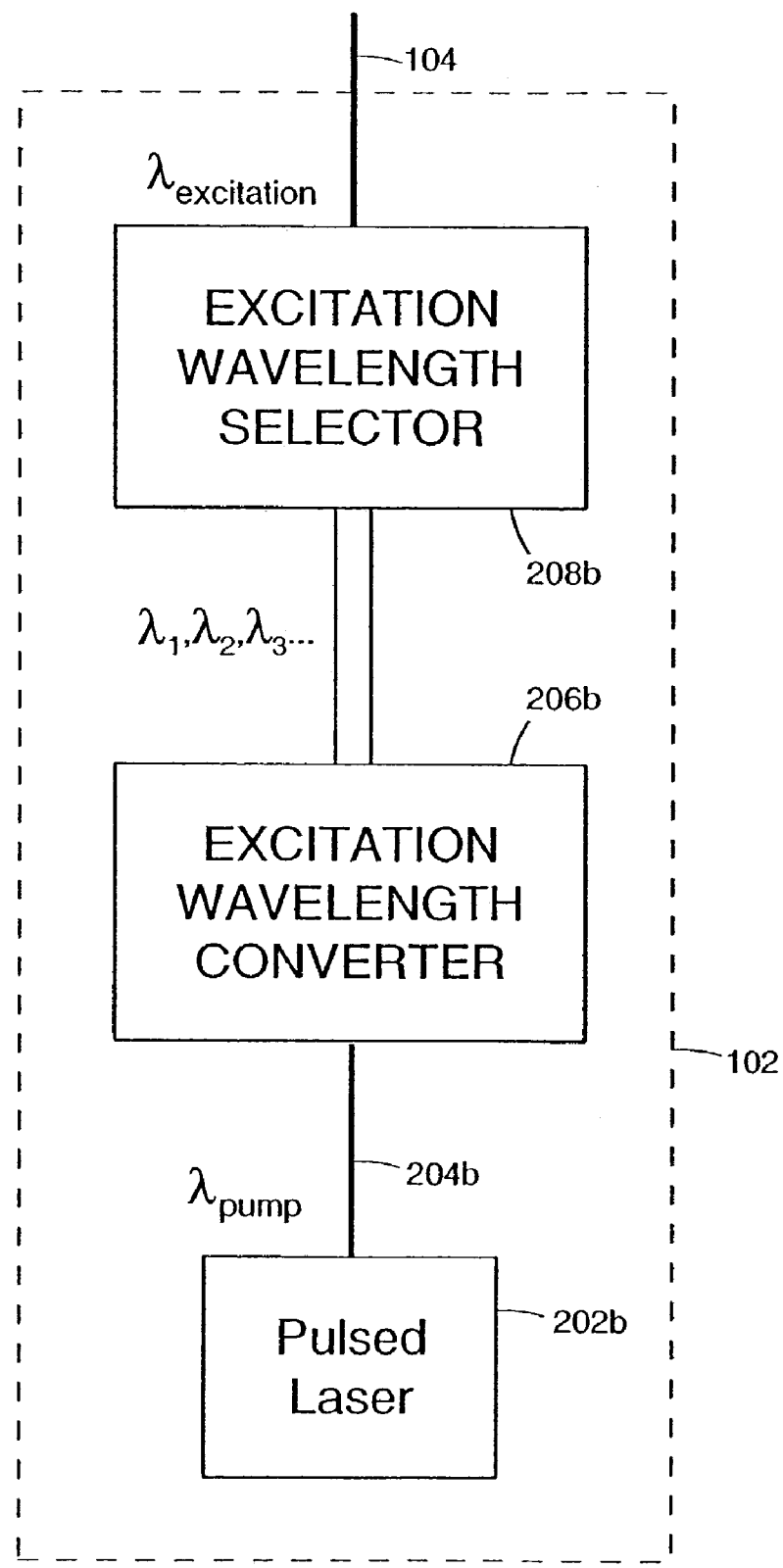

In another embodiment, demonstrated in FIG. 2b, pulsed light source 102 includes input pulsed laser 202b, excitation wavelength-converter 206b, and excitation wavelength-selector 208b. Excitation wavelength-converter 206b receives pump beam 204b from input pulsed laser 202b and generates photons simultaneously at multiple wavelengths, $\lambda_1, \lambda_2, \lambda_3$, etc. when pumped by pump beam 204b (or a portion of pump beam 204b). Excitation wavelength-converter 206b transmits the photons at the multiple wavelengths to excitation wavelength-selector 208b. Excitation wavelength-selector 208b receives the photons at the multiple wavelengths from excitation wavelength-converter 206b and serves to restrict the output to one wavelength ($\lambda_{excitation}$) at a time in beam 104.

In one embodiment, excitation wavelength-converter 206b includes a Raman shifting cell for generating photons simultaneously at a number of different wavelengths. The action of wavelength-selector 208b can be accomplished with a prism, a monochromator, a series of filters, or the like. Input pulsed laser 202b can be a single-mode pulsed laser, e.g., the passively Q-switched, solid-state Nd: YAG laser manufactured by Litton Airtron Synoptics (Model ML-00024).

Beam 104 irradiates sample 108, which contains a fluorescent compound or mixture of fluorescence compounds, including, but not limited to, aromatic hydrocarbons, chlorophyll, fluorescent tracer dyes, DNA or RNA molecules reacted with a fluorescent tag, etc. In another embodiment, beam 104 is focused on sample 108 with a lens, a curved mirror, or other optic that serves to concentrate the light beam. Beam 104 irradiates sample 108, causing sample 108 to emit fluorescence beam 110. Fluorescence beam 110 consists of a repetitive stream of fluorescence pulses, one fluorescence pulse being generated for each excitation light pulse that strikes sample 108. Fluorescence beam 110 is directed to photodetector 126. In one embodiment fluorescence wavelength selector 118 is interposed between the fluorescence beam 110 and the photodetector 126. In one embodiment, the fluorescence beam 110 passes through lens 112 that concentrates fluorescence beam 110 onto fluorescence wavelength selector 118. In another embodiment, fluorescence beam 110 from sample 108 is directed to the fluorescence wavelength selector via an optical fiber 114. In another embodiment, the lens 112 and optical fiber 114 are used together, as demonstrated in FIG. 1.

In another embodiment, beam 104 passes through waveplate 106 before arriving at sample 108. Waveplate 106 rotates or changes the polarization properties of beam 104. This enables light beams of different excitation polarizations to be applied to sample 108. For one embodiment, waveplate 106 is a half-waveplate for rotating a polarization angle, e.g., to various angles from a horizontal polarization angle to a vertical polarization angle.

For another embodiment, a polarizer (or emission polarizer) 116, such as a film or prism polarizer or the like, is interposed between sample 108 and photodetector 126. For one embodiment, polarizer 116 is oriented at a first polarization angle, such as 54.7 degrees, relative to the plane of polarization of beam 104, e.g., for removing transient effects associated with collisions that reorient the direction of the fluorescing molecules transition dipole. For some embodiments, polarizer 116 is oriented at other polarization angles for collecting fluorescence waveforms at these polarization angles. This enables determination of a rotational correlation time and a transition anisotropy. The rotational correlation time is the characteristic time interval over which the orientation of the fluorescing molecules becomes randomized. For one embodiment, florescence from sample 108 is measured with polarizer 116 oriented parallel and then perpendicular to the polarization of beam 104 to study and analyze or to determine the rotational correlation and anisotropy.

Fluorescence wavelength-selector 118 receives as an input fluorescence beam 110. Fluorescence wavelength-selector 118 outputs a substantial portion of the input fluorescence that lies within a specified wavelength range as beam $120_j$ (where j, an index running from 1 to N, labels the various possible emission wavelengths that can be selected). It will be appreciated by those of ordinary skill in the art of fluorescence that stream $120_j$ comprises fluorescence photons whose wavelengths lie in a range about a center wavelength $\lambda_j$.

In embodiments involving variation of the fluorescence emission wavelength for purposes of generating an emission wavelength-time matrix, fluorescence wavelength-selector 118 sequentially outputs beams $120_j$, $120_k$, etc. at two or more emission wavelengths $\lambda_j$, $\lambda_k$, etc. In embodiments where pulsed light source 102 selectively outputs beam 104 at two or more excitation wavelengths for purposes of generating an excitation wavelength-time matrix, fluorescence wavelength-selector 118 outputs stream $120_j$ at a single wavelength $\lambda_j$.

The specific values of emission wavelengths that are established by the emission wavelength selector 118 are selected per the particular application. For example, in applications involving fluorescent dye molecules deliberately added to the sample, the emission wavelength could be chosen after consideration of the known fluorescence spectra of the dye molecules. It will be appreciated by those of ordinary skill in the art that one might choose a different emission wavelength than the one at which intensity is greatest in order to minimize interference from scattered excitation photons or for other reasons.

Figure 3:
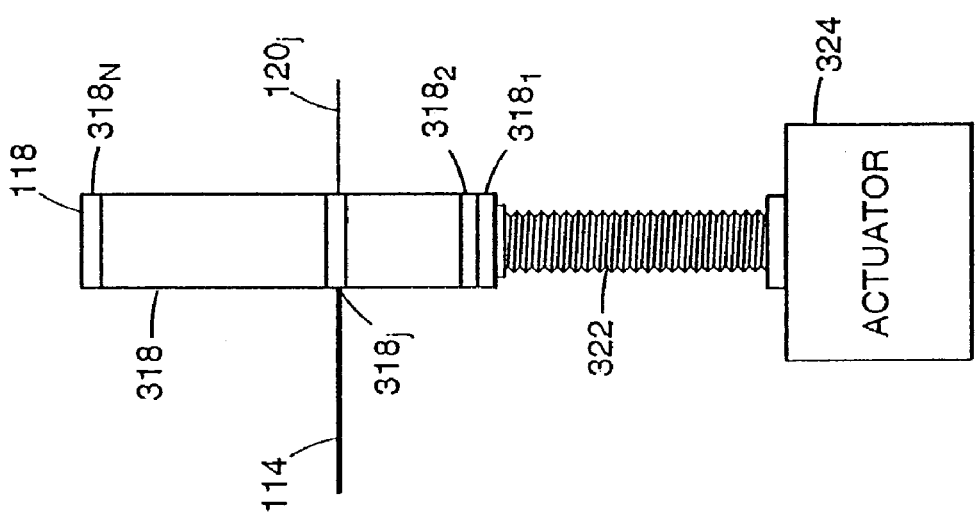

In one embodiment, fluorescence wavelength-selector 118 is a linear variable filter 318, as demonstrated in FIG. 3. The wavelength passband of linear variable filter 318 is continuously graded along its length, but it functions as if it contained a multitude of segments $318_j$, j=1 to N. Each segment $318_j$ allows fluorescence at substantially a single corresponding wavelength $\lambda_j$ to pass through it, thereby creating wavelength-selected fluorescence beam $120_j$. To select fluorescence at a wavelength $\lambda_j$ to be output from linear variable filter 318, linear variable filter 318 is positioned so that the appropriate section of the linear variable filter intercepts beam 110. In one embodiment, linear variable filter 318 is actuated using lead-screw 322 driven by actuator 324, e.g., a stepper motor, as shown in FIG. 3. In another embodiment, linear variable filter 318 passes wavelengths in the range of 380 to 720 nanometers.

In another embodiment, a control circuit that receives inputs from a computer program controls actuator 324. In this embodiment, the user selects a set of wavelengths, and actuator 324 positions linear variable filter 318 so that the selected wavelengths pass through the appropriate regions of linear variable filter 318. In another embodiment, the control circuit also receives inputs from light source 102. In this embodiment, the user selects the desired wavelengths and the number of light pulses for which data are to be collected at each wavelength. After the selected number of pulses is passed through the appropriate region of linear variable filter 318, actuator 324 positions the linear variable filter to isolate fluorescence light in a different desired wavelength range. This is repeated for each of the selected wavelengths.

Figure 4:
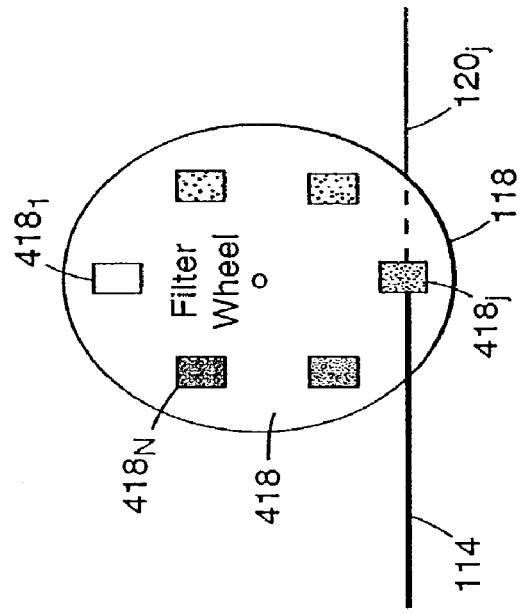
FIGS. 3, 4, and 5 respectively illustrate different embodiments of a fluorescence wavelength-selector according to the teachings of the present invention.

In other embodiments, fluorescence wavelength-selector 118 includes a set of discrete filters. In one embodiment, the set of discrete filters $418_1$ to $418_N$ is arranged in a holder that is able to position a desired discrete filter to select fluorescence photons emitted by the sample at a substantially single, corresponding wavelength. For example, in one embodiment, the discrete filters $418_1$ to $418_N$ are arranged on filter wheel 418, as demonstrated in FIG. 4. In one embodiment, the filters are chosen on the basis of the expected wavelength distribution of the total fluorescence emission. To select fluorescence at a wavelength $\lambda_j$ to be output from filter wheel 418, filter wheel 418 is actuated so that discrete filter $418_j$ receives a portion of the pulsed fluorescence contained in stream 110. The fluorescence having a wavelength $\lambda_j$ passes through discrete filter $418_j$ and is output as stream $120_j$. In one embodiment, filter wheel 418 is actuated using a stepper motor.

In another embodiment, fluorescence wavelength-selector 118 is an acousto-optic tunable filter. In another embodiment, fluorescence wavelength-selector 118 is a monochromator.

Figure 5:
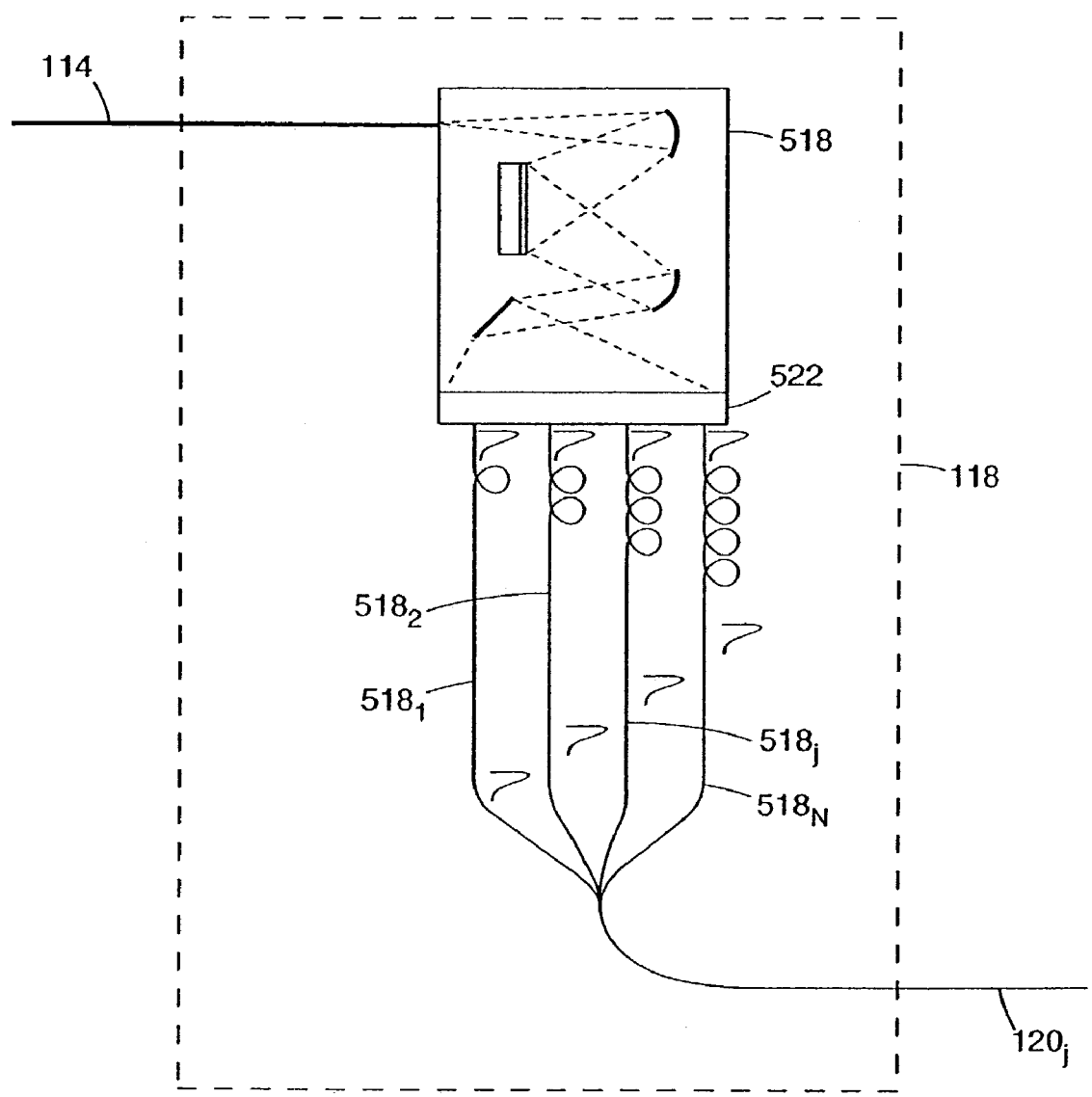

In another embodiment, fluorescence wavelength-selector 118 comprises spectrograph 518 and optical fibers $518_1$ to $518_N$, as shown in FIG. 5. Each of optical fibers $518_1$ to $518_N$ is coupled to transmit fluorescence photons at a substantially single wavelength from the position of the exit focal plane 522 of spectrograph 518 to photodetector 126 (see FIG. 1). Optical fibers $518_1$ to $518_N$ respectively output signals $120_1$ to $120_N$, which contain photons at the desired wavelengths $\lambda_1$ to $\lambda_N$.

Each of optical fibers $518_1$ to $518_N$ has a different length in order to temporally separate the arrival of photon signals $120_j$ at photodetector 126. For example, photon signal $120_1$ reaches the photodetector 126 earlier in time than photon signal $120_2$ because optical fiber $518_1$, is shorter than optical fiber $518_2$. It is in this way that the fluorescence wavelength is selected. Details of using a spectrograph and optical fibers for selecting wavelengths of fluorescence are described in U.S. Pat. No. 5,828,452, entitled SPECTROSCOPIC SYSTEM WITH A SINGLE CONVERTER AND METHOD FOR REMOVING OVERLAP IN TIME OF DIRECTED EMISSIONS, issued on Oct. 27, 1998, which is incorporated herein by reference.

Focusing on the jth wavelength, where j can be any of one or more integer values between 1 and N, photodetector 126 receives beam $120_j$ as an input from fluorescence wavelength-selector 118, as demonstrated in FIG. 1. Photodetector 126 converts beam $120_j$ into time-dependent analog electrical signal 128j and outputs time-dependent analog electrical signal 128j. In other embodiments, photodetector 126 is a photomultiplier tube, multianode photomultiplier tube, a microchannel plate photomultiplier tube, a photodiode, an avalanche photodiode, or the like.

Signal processor 130 receives time-dependent analog electrical signal 128j as an input. More specifically, digitizer 132 of signal processor 130 receives analog time-dependent electrical signal $128_j$ as an input.

Figure 7:
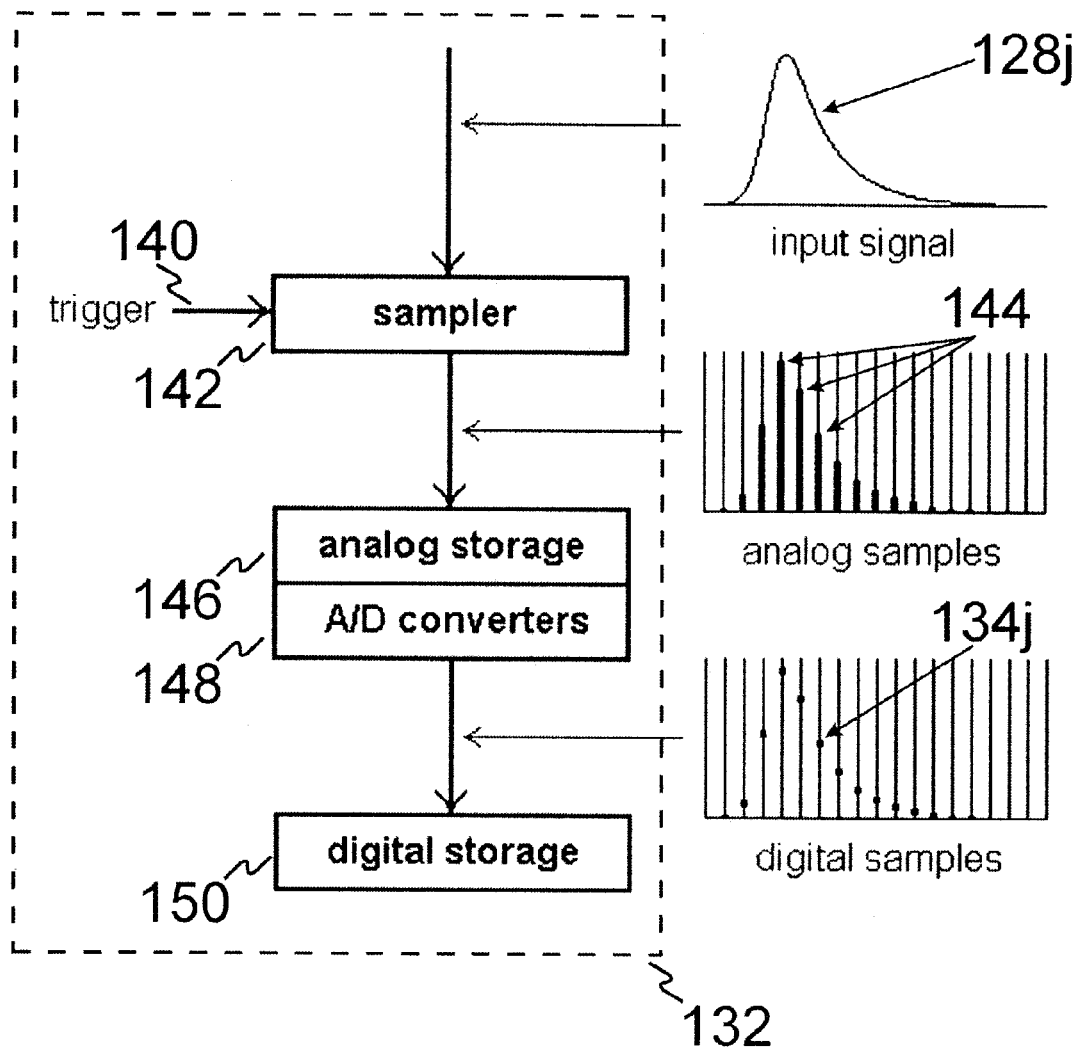
FIG. 7 illustrates a digitizer according to an embodiment of the present invention.

FIG. 7 illustrates digitizer 132 according to another embodiment of the present invention. Digitizer 132 includes a sampler 142 that samples time-dependent analog electrical signal $128_j$. For one embodiment, a trigger signal 140 activates sampler 142. For another embodiment, sampler 142 generates one or more sampling strobes in response to receiving trigger signal 140. Each sampling strobe causes sampler 142 to obtain a sample 144 of signal $128_j$ and store the sample 144 in analog memory (or storage) 146. Each sample 144 is a voltage or a charge that is proportional to signal $128_j$. For some embodiments, analog memory 146 includes an array of memory elements (not shown), such as capacitors, that stores a representation of time-dependent electrical signal $128_j$ as a time-series of analog voltages or charges. Specifically, each element of the array stores a sample 144. For other embodiments, successive elements in the array correspond to a time increment no greater than 1 ns. For one embodiment, an A/D converter 148 is coupled to analog memory 146. A/D converter 148 operates on the analog data in analog memory 146 to generate the digital fluorescence decay waveform representation $134_j$ that is stored in digital memory 150. For some embodiments, there is a single A/D converter for a single array, a single A/D converter for each element of the array, etc.

For another embodiment, multiple input signals are received at digitizer 132. For this embodiment, each strobe causes sampler 142 to obtain a sample of each of the input signals and store the samples in analog memory 146. In one embodiment, analog memory 146 has a plurality of arrays each of which receives samples from a respective one of the input signals. There can be a single A/D converter for each of arrays or a single A/D converter for all of the arrays, etc. For one embodiment, the multiple input signals are copies of each other and are delayed in time relative to each other. For another embodiment, each of the multiple input signals are amplified or attenuated.

Recorder 136 receives digitized fluorescence decay curves $134_j$ from digitizer 132 for at least two emission wavelengths or at least two excitation wavelengths or at least two fluorescence polarizer orientations relative to a polarization of the excitation pulse and records and outputs a parameter-time matrix of digitized fluorescence waveforms. For one embodiment, the parameter-time matrix is an emission wavelength-time matrix, an excitation wavelength-time matrix, or a polarizer-orientation-time matrix.

In embodiments in which fluorescence wavelength selector 118 outputs a single wavelength at a time, digitized signal $134_j$ comprises a digitized fluorescence decay curve corresponding to emission wavelength $\lambda_j$. A digitized fluorescence decay curve is acquired for every pulse of pulsed light source 102. In embodiments involving variation of the emission wavelength for purposes of generating an emission wavelength-time matrix, recorder 136 receives digitized fluorescence decay curves $134_j$ from digitizer 132 for at least two emission wavelengths and outputs an emission wavelength-time matrix. In one embodiment, recorder 136 averages the digital fluorescence decay curves at each j-value (emission wavelength) by summing the digital fluorescence decay curves for multiple laser shots and dividing the summed fluorescence decay curve by the number of laser shots. The output of recorder 136, which then comprises an emission wavelength-time matrix that includes averaged fluorescence decay curves for at least two emission wavelengths, is suitable for subsequent mathematical processing and analysis.

In the embodiment of FIG. 5, digitized signal 134 incorporates the fluorescence decay curves for a series of emission wavelengths $\lambda_j$, the component fluorescence decay curves separated in time from each other by the delays created by light traveling over the optical fibers $518_1$ to $518_N$. In one embodiment, recorder 136 averages the digital fluorescence decay curves that contain contributions for several emission wavelengths by summing the digital fluorescence decay curves for multiple laser shots and dividing the summed fluorescence decay curve by the number of laser shots. The output of recorder 136 can then be processed to generate an emission wavelength-time matrix that includes averaged fluorescence decay curves for at least two emission wavelengths and is suitable for subsequent mathematical processing and analysis. The means by which the emission wavelength-time matrix is generated by removing the delays imposed by the fiber optic delay line is described U.S. Pat. No. 5,828,452, entitled SPECTROSCOPIC SYSTEM WITH A SINGLE CONVERTER AND METHOD FOR REMOVING OVERLAP IN TIME OF DIRECTED EMISSIONS, issued on Oct. 27, 1998, which is incorporated above by reference. In another embodiment, the digital fluorescence decay curves that contain contributions for several emission wavelengths can be analyzed directly by a basis set method.

In embodiments where pulsed light source 102 selectively outputs beam 104 at two or more excitation wavelengths for purposes of generating an excitation wavelength-time matrix, recorder 136 receives digitized signal $134_j$ from digitizer 132 at a single emission wavelength $\lambda_j$, and outputs an excitation wavelength-time matrix that includes fluorescence decay curves for at least two excitation wavelengths. In one embodiment, recorder 136 averages the digital fluorescence decay curves at each excitation wavelength by summing the digital fluorescence decay curves for multiple laser shots and dividing the summed fluorescence decay curve by the number of laser shots. The output of recorder 136, which then comprises an excitation wavelength-time matrix that includes averaged fluorescence decay curves for at least two excitation wavelengths, is suitable for subsequent mathematical processing and analysis.

In other embodiments, polarizer 116 selectively outputs a beam at two or more polarizer orientations for purposes of generating a polarizer-orientation-time matrix. For this embodiment, recorder 136 receives digitized signal $134_j$ from digitizer 132 at a single emission wavelength $\lambda_j$ and outputs a polarizer-orientation-time matrix that includes fluorescence decay curves for at least two polarizer orientations. In one embodiment, recorder 136 averages the digital fluorescence decay curves at each polarizer orientation by summing the digital fluorescence decay curves for multiple laser shots and dividing the summed fluorescence decay curve by the number of laser shots. The output of recorder 136, which then comprises a polarizer-orientation-time matrix that includes averaged fluorescence decay curves for at least two polarizer orientations, is suitable for subsequent mathematical processing and analysis.

Sample 108 should not be interpreted to mean a substance of invariant composition. The composition and nature of sample 108 could vary in time, as in the case of material eluting from the column in high performance liquid chromatography (HPLC), or as the sample undergoes chemical reaction. In other embodiments, sample 108 actually represents a set of soil samples probed at different depths below the ground surface, a set of discrete samples residing in the wells of a microplate, a set of various locations on a more or less flat surface, etc. In these cases, a parameter-time matrix can be acquired and processed for each member of the data set, e.g., parameter-time matrices are repetitively acquired, each individual parameter-time matrix being labeled by an index corresponding to various elution times, depths below ground surface, wells in a microplate, position on a surface, etc.

Figure 6:
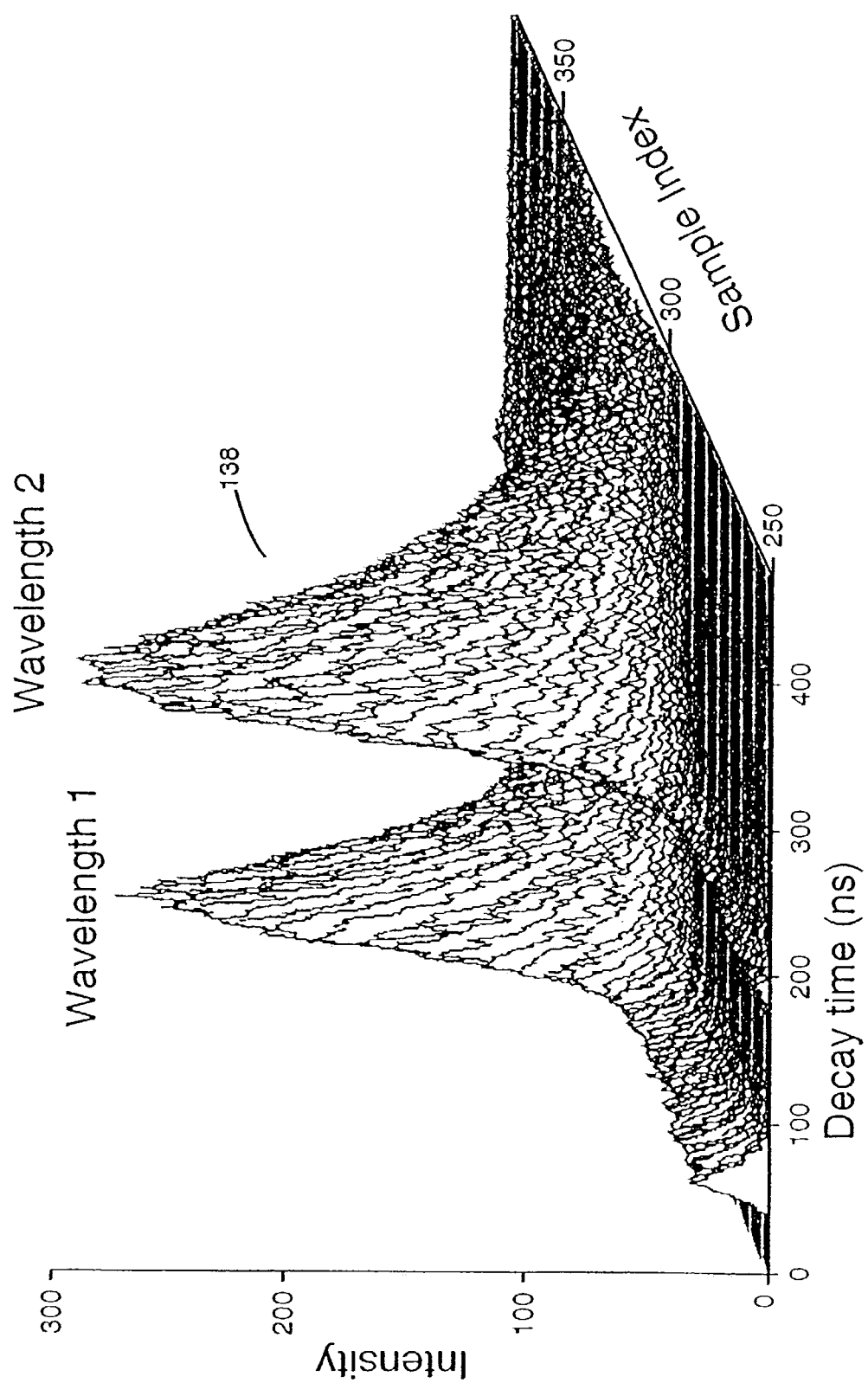
FIG. 6 is a graphical representation of an exemplary set of wavelength-time matrices according to the teachings of the present invention.

Plot 138, shown in FIGS. 1 and 6, is a graphical representation of an exemplary set of parameter-time matrices, e.g., wavelength-time matrices, for HPLC. Plot 138 is intended as an example and can be viewed as a graphical representation of an embodiment in which the emission wavelength-time matrix is encoded in a single intensity vs. time record via the use of fiber optic delay lines. The different sample indices correspond to different elution times.

Analyzer 140 of signal processor 130 receives the parameter-time matrix from the recorder and outputs a numerical value for the contribution of at least one fluorescent component to the data contained within the parameter-time matrix (excitation or emission wavelength or polarizer orientation). In one embodiment, analyzer 140 is a computer program, e.g., MATLAB, that implements an algorithm, e.g., the SIMPLEX algorithm, to interpret the data contained within the parameter-time matrix.

The parameter-time matrix can be represented as an m×n matrix [D], where m is the number of rows in the matrix and n is the number of columns in the matrix. In one embodiment, m is the number of decay time increments for each fluorescence decay curve and n is the number of emission wavelengths. In another embodiment, m is the number of decay time increments for each fluorescence decay curve and n is the number of excitation wavelengths. For yet another embodiment, m is the number of decay time increments for each fluorescence decay curve and n is the number of polarizer orientations. For purposes of the analysis, matrix [D] can be represented as a product of two matrices $$[D]=[A]\times[C] \quad (1)$$

where [A] is an m x p matrix whose columns contain fluorescence spectra of the p emitting components in sample 108 and [C] is an p×n matrix whose rows contain fluorescence decay curves for the p emitting components. The product representation shown in equation (1) is based on the assumptions of linear detector response and independent response of each component in the sample.

By decomposing matrix [D] into components [A] and [C], analyzer 140 identifies the individual components of sample 108 and constructs representations of their fluorescence spectra and decay kinetics. In one embodiment, analyzer 140 decomposes matrix [D] by constructing a model matrix [D'] as in equation (2)

$$[D']=[A']\times[C'] \quad (2)$$

In one embodiment, analyzer 140 constructs [C'] row by row using equation (3) below $$C'_{s,r} \sum_{q=1}^{r} E_q \exp\left(-(r-q)\frac{\Delta t}{\tau_s}\right) \quad (3)$$

where q represents the $q^{th}$ digitization interval, $E_q$ is the intensity of a pulse of beam 104 at the $q^{th}$ digitization interval, $\tau_s$ is the lifetime of the $s^{th}$ component of sample 108, and $\Delta t$ is the digitization time interval. Analyzer 140 calculates the components [C'] based on a trial set of $\tau_s$ values.

Analyzer 140 determines [A'] from $$[A']=[D][C']^T([C'][C']^T)^{-1} \quad (4)$$

where superscript T refers to the transpose of the corresponding matrix.

Analyzer 140 determines [D'] from equation (2) using [C'] and [A']. Analyzer 140 compares [D'] to [D] by computing the sum of the square of the differences between the components of [D'] and the corresponding components of [D] from $$\chi^2 = \sum_{q=1}^{m}\sum_{r=1}^{n}(D_{q,r}-D'_{q,r})^2 \quad (5)$$

where $D_{q,r}$ and $D'_{q,r}$ are respectively the q–r components of [D] and [D'] Note that the value of $\chi^2$ depends the trial set of $\tau_s$ values. Analyzer 140 varies the trial set of $\tau_s$ values until $\chi^2$ is minimized.

When $\chi^2$ is minimized, the corresponding set of $\tau_s$ values represents the lifetimes of the respective components of sample 108. Moreover, the [A] matrix corresponding to the minimum value for $\chi^2$ gives the spectra of the respective components of sample 108 multiplied by scaling factors that are related to the concentrations of the components.

In embodiments where sample 108 is changing, it is convenient and appropriate to collect a series of parameter-time matrices, one for each discrete sample, elution time, depth, location on a surface, etc. Each element in the series shall be referred to as a sub-sample. The parameter-time matrix for each sub-sample can be independently analyzed in the fashion described above. However, a given component could be present in many, perhaps even all, of the sub-samples. The fluorescence spectrum and lifetime for a component is not expected to change from one sub-sample to another, but its concentration does.

In one embodiment, parameter-time matrices are measured for reference samples of known composition. The measured parameter-time matrices can be represented as a linear combination of the reference parameter-time matrices with a non-negative least squares fit algorithm.

In another embodiment, analyzer 140 writes each parameter-time matrix obtained from sample 108 as a single column vector d. In one embodiment, the parameter-time matrix obtained from sample 108 is an emission wavelength-time matrix. In another embodiment, the parameter-time matrix obtained from sample 108 is an excitation wavelength-time matrix. For other embodiments, the parameter-time matrix is a polarizer-orientation-time matrix. Analyzer 140 then expresses column vector d as the product of an unknown column vector c and matrix [B] as in equation (6)

$$d=c\times[B] \quad (6)$$

In equation (6), matrix [B] is a measured parameter-time matrix for a set of target compounds.

Each column of matrix [B] is a decay profile of one of the target compounds. Each decay profile is obtained by replacing sample 108 in apparatus 100 with a target compound. Each target compound is either known or suspected to be present in sample 108.

In other embodiments, the first column of [B] is a background profile scaled to an intensity that is comparable to the other columns of [B]. The background profile is chosen by examining the complete data set for parameter-time matrices of sub-samples that have the lowest intensities. The parameter-time matrices for these low intensity samples are averaged and the average is taken as the background profile.

Analyzer 140 solves equation (6) to produce a set of coefficients in vector c that indicate how much of each decay profile from [B] is needed to produce the observed decay profile of vector d. This enables the identification of the compounds in sample 108 and their concentration. In one embodiment, analyzer 140 uses a curve fitting procedure to replicate an observed decay profile based on decay profiles for the reference compounds that could be in the mixture. In another embodiment, analyzer 140 uses a non-negative least squares approach to find the values for the vector c. Details of forming matrix [B] and solving equation (6) using a non-negative least squares approach to find the values for the vector c are given in U.S. Pat. No. 5,828,452, entitled SPECTROSCOPIC SYSTEM WITH A SINGLE CONVERTER AND METHOD FOR REMOVING OVERLAP IN TIME OF DIRECTED EMISSIONS, issued on Oct. 27, 1998, which is incorporated above by reference.

CONCLUSION

Embodiments of the present invention have been described. The embodiments provide a means of generating fluorescence decay curves and second-order parameter-time matrices at a level of speed and precision heretofore unavailable.

Although specific embodiments have been illustrated and described in this specification, it will be appreciated by those of ordinary skill in the art that any arrangement that is calculated to achieve the same purpose may be substituted for the specific embodiment shown. This application is intended to cover any adaptations or variations of the present invention.

What is claimed is:

1. An apparatus that provides rapid and sensitive quantitative analysis of a sample's fluorescence decay properties, the apparatus comprising:
   a repetitively pulsed excitation light source for generating excitation light pulses, an output of which generates pulsed fluorescence in the sample;
   a fluorescence wavelength selector that receives as input a portion of the pulsed fluorescence emanating from the sample and that outputs fluorescence photons whose wavelengths lie within a specified wavelength range, said selector being configured to select two or more wavelength ranges;
   a photodetector that receives the fluorescence photons within a specified wavelength range as an input from the fluorescence wavelength selector and outputs a time-dependent electrical signal;
   an array of memory elements that stores a representation of the time-dependent electrical signal as a time-series of analog voltages or charges, wherein successive elements in the array correspond to samples of the time-dependent electrical signal with a time increment of no greater than 4 ns;
   an analog-to-digital converter that transforms the time-series of analog voltages or charges into a corresponding sampled and digitized fluorescence wave form; and
   means for storing two or more sampled and digitized waveforms as a multidimensional parameter-time matrix with the waveforms representing at least two wavelengths selected for the photodetector by the fluorescence wavelength selector.

2. The apparatus of claim 1, wherein a duration of the excitation light pulses is less than 1 ns.

3. The apparatus of claim 1, wherein the light source is adapted to emit 100 or more pulses each second.

4. The apparatus of claim 1, wherein the light source is at least one of a pulsed laser, a pulsed laser that is passively Q-switched, and a pulsed laser that is single mode.

5. The apparatus of claim 1, wherein the fluorescence wavelength-selector comprises a linear variable filter.

6. The apparatus of claim 5, wherein the fluorescence wavelength-selector further comprises an actuator that is coupled to the linear variable filter and that moves the linear variable filter so as to vary the wavelength of fluorescence transmitted by the linear variable filter within the specified wavelength range.

7. The apparatus of claim 1, wherein the fluorescence wavelength-selector comprises a set of discrete filters, each of the discrete filters of the set serving to transmit fluorescence photons emitted by the sample at a different wavelength.

8. The apparatus of claim 7, wherein the set of discrete filters is arranged in a holder that positions individually each of the discrete filters to select fluorescence photons emitted by the sample in the specified wavelength range.

9. The apparatus of claim 1, wherein the fluorescence wavelength-selector comprises one of an acousto-optic tunable filter, a monochromator, and a spectrograph.

10. The apparatus of claim 1, wherein the fluorescence wavelength-selector comprises a spectrograph and a plurality of optical fibers each coupled to transmit fluorescence photons from an exit focal plane of the spectrograph to the photodetector, each fiber transmitting a different wavelength of the specified wavelength range, the fibers having different lengths to temporally separate the arrival of the fluorescence photons of the different wavelengths at the photodetector.

11. The apparatus of claim 1, wherein the photodetector comprises one of a photomultiplier tube, a multianode photomultiplier tube, a microchannel plate photomultiplier tube, a photodiode, and an avalanche photodiode.

12. The apparatus of claim 1, wherein optical elements are used to concentrate the light emitted from the sample onto the fluorescence wavelength-selector.

13. The apparatus of claim 1, wherein the light source comprises an input pulsed laser and an excitation wavelength-converter for selectively outputting the excitation light pulses at various excitation wavelengths.

14. The apparatus of claim 1, wherein the light source comprises an input pulsed laser, excitation wavelength-converter, and excitation wavelength-selector for selectively outputting the excitation light pulses at various excitation wavelengths.

15. The apparatus of claim 1, and further comprising a polarizer disposed between the sample and the photodetector.

16. The apparatus of claim 1, and further comprising a waveplate disposed between the pulsed light source and the sample.

17. An apparatus that provides rapid and sensitive quantitative analysis of a sample's fluorescence decay properties, the apparatus comprising:
   a repetitively pulsed excitation light source for generating excitation light pulses, the output of which generates pulsed fluorescence in the sample;
   a fluorescence wavelength selector that receives as input a portion of the pulsed fluorescence emanating from the sample and that outputs fluorescence photons whose wavelengths lie within a specified range, said selector being configured to select two or more wavelength ranges;
   a photodetector that receives the fluorescence photons within the specified wavelength range as an input from the fluorescence wavelength selector and outputs a time-dependent electrical signal corresponding to fluorescence intensity;
   an array of memory elements that stores a representation of the time-dependent electrical signal as a time-series of analog voltages or charges, wherein successive elements in the array correspond to a time increment of no greater than 4 ns, said array being configured to receive and store a time series of analog voltages or charges representing substantially all of the rise and decay of the time-dependent electrical signal resulting from at least one excitation light pulse;
   an analog-to-digital converter that transforms the time-series of analog voltages or charges into a corresponding digitized fluorescence waveform;
   a recorder that receives digitized fluorescence waveforms from the analog-to-digital converter and outputs a two dimensional parameter-time matrix, said matrix containing intensity data representing fluorescence decay curves for at least two emission wavelengths or at least two excitation pulses that differ in wavelength or in polarizer orientations relative to a polarization of the excitation pulse;

and an analyzer that receives the parameter-time matrix from the recorder and outputs a numerical value for the quantitative contribution of at least one fluorescent component to the intensity data contained within the two-dimensional parameter-time matrix.

18. The apparatus of claim 17, wherein a duration of the excitation light pulses is less than 1 ns.

19. The apparatus of claim 18, wherein the fluorescence wavelength-selector further comprises an actuator that is coupled to the linear variable filter and that moves the linear variable filter so as to vary the wavelength of fluorescence transmitted by the linear variable filter within the specified wavelength range.

20. The apparatus of claim 17, wherein the light source is adapted to emit 100 or more pulses each second.

21. The apparatus of claim 17, wherein the light source is at least one of a pulsed laser, a pulsed laser that is passively Q-switched, and a pulsed laser that is single mode.

22. The apparatus of claim 17, wherein the fluorescence wavelength-selector comprises a linear variable filter.

23. The apparatus of claim 17, wherein the fluorescence wavelength-selector comprises a set of discrete filters, each of the discrete filters of the set serving to transmit fluorescence photons emitted by the sample at a different wavelength.

24. The apparatus of claim 23, wherein the set of discrete filters is arranged in a holder that positions individually each of the discrete filters to select fluorescence photons emitted by the sample in the specified wavelength range.

25. The apparatus of claim 17, wherein the fluorescence wavelength-selector comprises one of an acousto-optic tunable filter, a monochromator, and a spectrograph.

26. The apparatus of claim 17, wherein the fluorescence wavelength-selector comprises a spectrograph and a plurality of optical fibers each coupled to transmit fluorescence photons from an exit focal plane of the spectrograph to the photodetector, each fiber transmitting a different wavelength of the specified wavelength range, the fibers having different lengths to temporally separate the arrival of the fluorescence photons of the different wavelengths at the photodetector.

27. The apparatus of claim 17, wherein the photodetector comprises one of a photomultiplier tube, a multianode photomultiplier tube, a microchannel plate photomultiplier tube, a photodiode, and an avalanche photodiode.

28. The apparatus of claim 17, wherein optical elements are used to concentrate the light emitted from the sample onto the fluorescence wavelength-selector.

29. The apparatus of claim 17, wherein the light source comprises an input pulsed laser and an excitation wavelength-converter for selectively outputting the excitation light pulses at various excitation wavelengths.

30. The apparatus of claim 17, wherein the light source comprises an input pulsed laser, excitation wavelength-converter, and excitation wavelength-selector for selectively outputting the excitation light pulses at various excitation wavelengths.

31. The apparatus of claim 17, and further comprising a polarizer disposed between the sample and the photodetector.

32. The apparatus of claim 17, and further comprising a waveplate disposed between the pulsed light source and the sample.

33. A fluorometric method comprising:

irradiating a sample with a plurality of light pulses that excite pulsed fluorescence in the sample;

selecting a portion of the pulsed fluorescence from the sample within a specified wavelength range;

generating a time-dependent electrical signal based on the selected portion of the pulsed fluorescence;

storing a representation of the time-dependent electrical signal as a time-series of analog voltages or charges in an array of memory elements, wherein successive elements in the array correspond to a time increment of no greater than 4 ns;

converting the time-series of analog voltages or charges into a corresponding digitized fluorescence waveform;

recording a parameter-time matrix of digitized fluorescence waveforms for at least two emission wavelengths or at least two excitation pulses that differ in wavelengths or in polarizer orientations relative to a polarization of the excitation pulse; and analyzing the data in the parameter-time matrix to determine a numerical value of a concentration, fluorescence lifetime, or rotational correlation time for at least one fluorescent component in the sample.

34. The method of claim 33, wherein analyzing the parameter-time matrix comprises using reference parameter-time matrices for target compounds.

35. The method of claim 34, wherein analyzing the parameter-time matrix comprises fitting the reference parameter-time matrices to the parameter-time matrix using a non-negative least squares method.

36. The method of claim 34, wherein analyzing the parameter-time matrix comprises representing the data contained within the parameter-time matrix as a product of two matrices, such that one matrix contains information on the wavelength or polarization dependence of the fluorescence of chemical components in the sample and the other matrix contains information on the fluorescence decay properties of the chemical components in the sample.

* * * * *